United States Patent [19]

Di Giovanni et al.

[11] Patent Number: 4,471,781

[45] Date of Patent: Sep. 18, 1984

[54] SURGICAL INSTRUMENT WITH ROTATABLE FRONT HOUSING AND LATCH MECHANISM

[75] Inventors: John Di Giovanni, Irvington; Glen C. Dorband, Somerville; Donald M. Golden, Cherry Hill, all of N.J.; William P. Mc Vay, Clearwater, Fla.

[73] Assignee: Ethicon, Inc., Somerville, N.J.

[21] Appl. No.: 345,307

[22] Filed: Feb. 3, 1982

[51] Int. Cl.³ .............................................. A61B 17/00
[52] U.S. Cl. ................................ 128/334 R; 128/339; 128/340
[58] Field of Search .................... 128/334 C, 335, 337, 128/339, 340; 604/902, 57-64; 433/91-99; 128/334 R

[56] References Cited

U.S. PATENT DOCUMENTS 2,393,910  1/1946  Karle .................................... 128/340

4,154,239  5/1979  Turley ................................... 604/62

Primary Examiner—C. Fred Rosenbaum
Assistant Examiner—Gene B. Kartchner
Attorney, Agent, or Firm—Robert L. Minier

[57] ABSTRACT

A structure is provided for accommodating the rotation of a front housing of an instrument to a selected position relative to the rear housing of the instrument to permit an operating member in the front housing to be located in a desired orientation. The front housing has an annular portion in which a cylindrical portion of the rear housing is received to permit the two housings to be rotated relative to each other about a common longitudinal axis. The front housing annular portion defines a plurality of bores arranged at selected azimuthal locations about the axis of rotation and the rear housing carries a reciprocative engaging member adapted to be moved partially into one of the bores to lock the two housings in a selected relative orientation.

2 Claims, 18 Drawing Figures

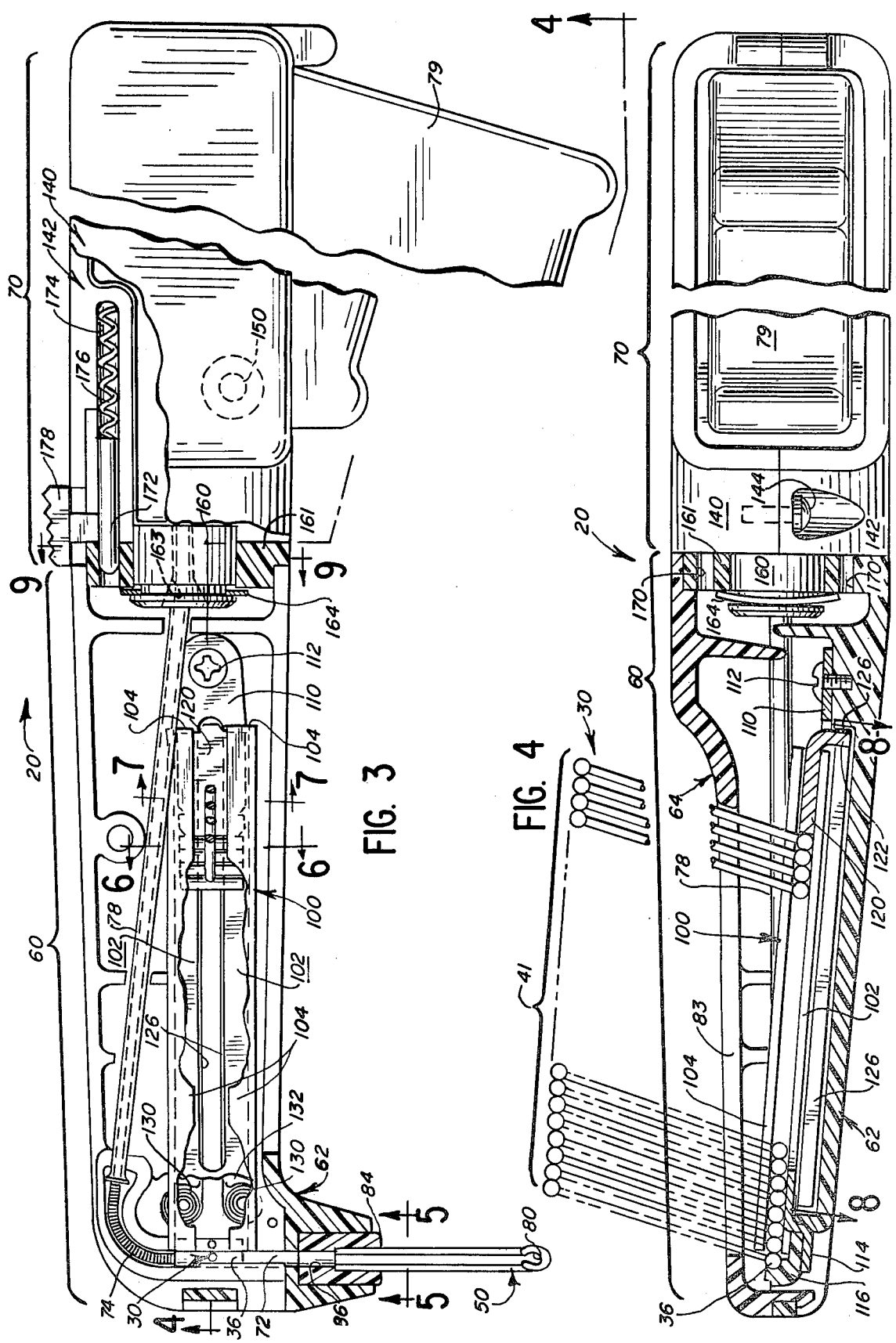

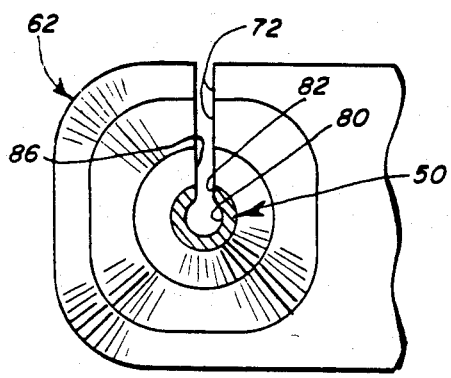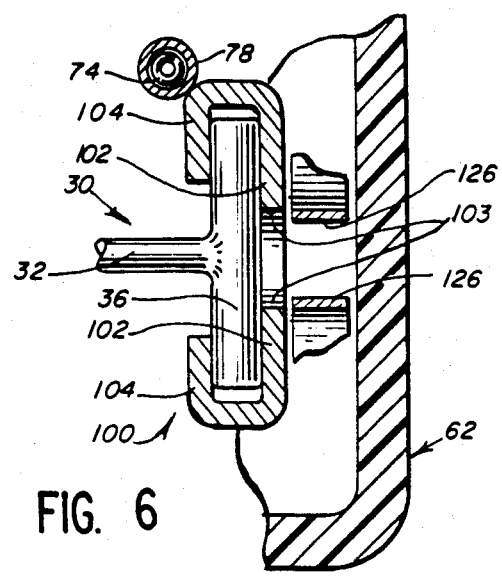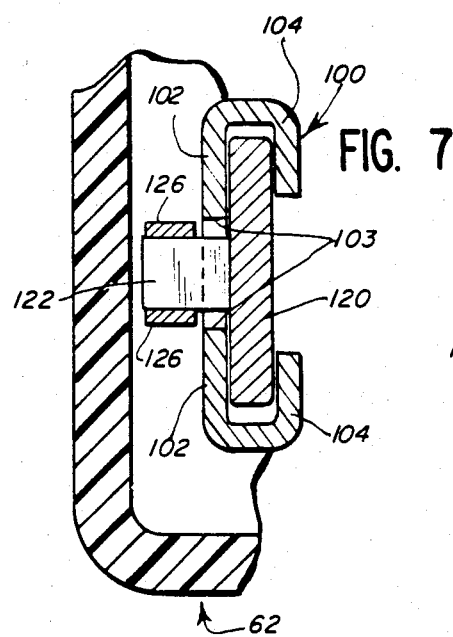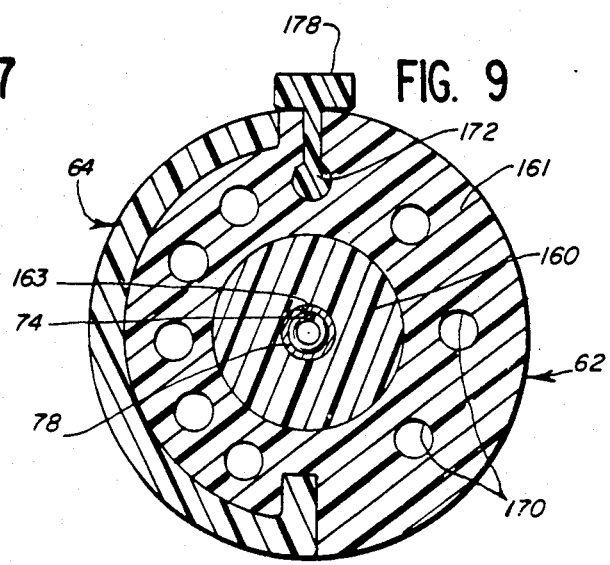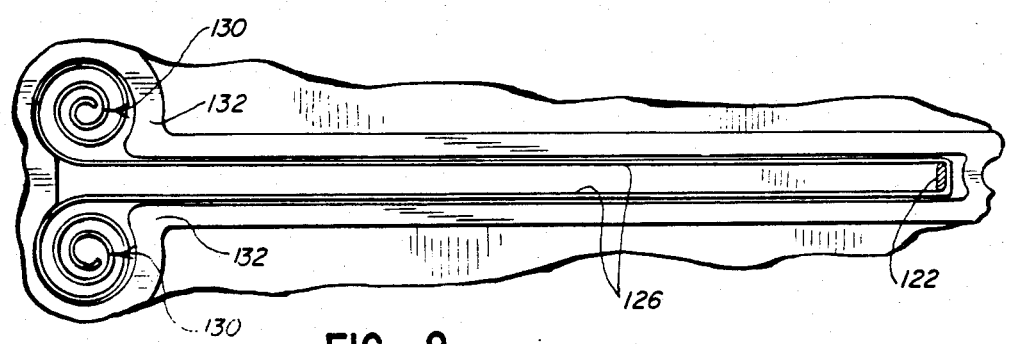

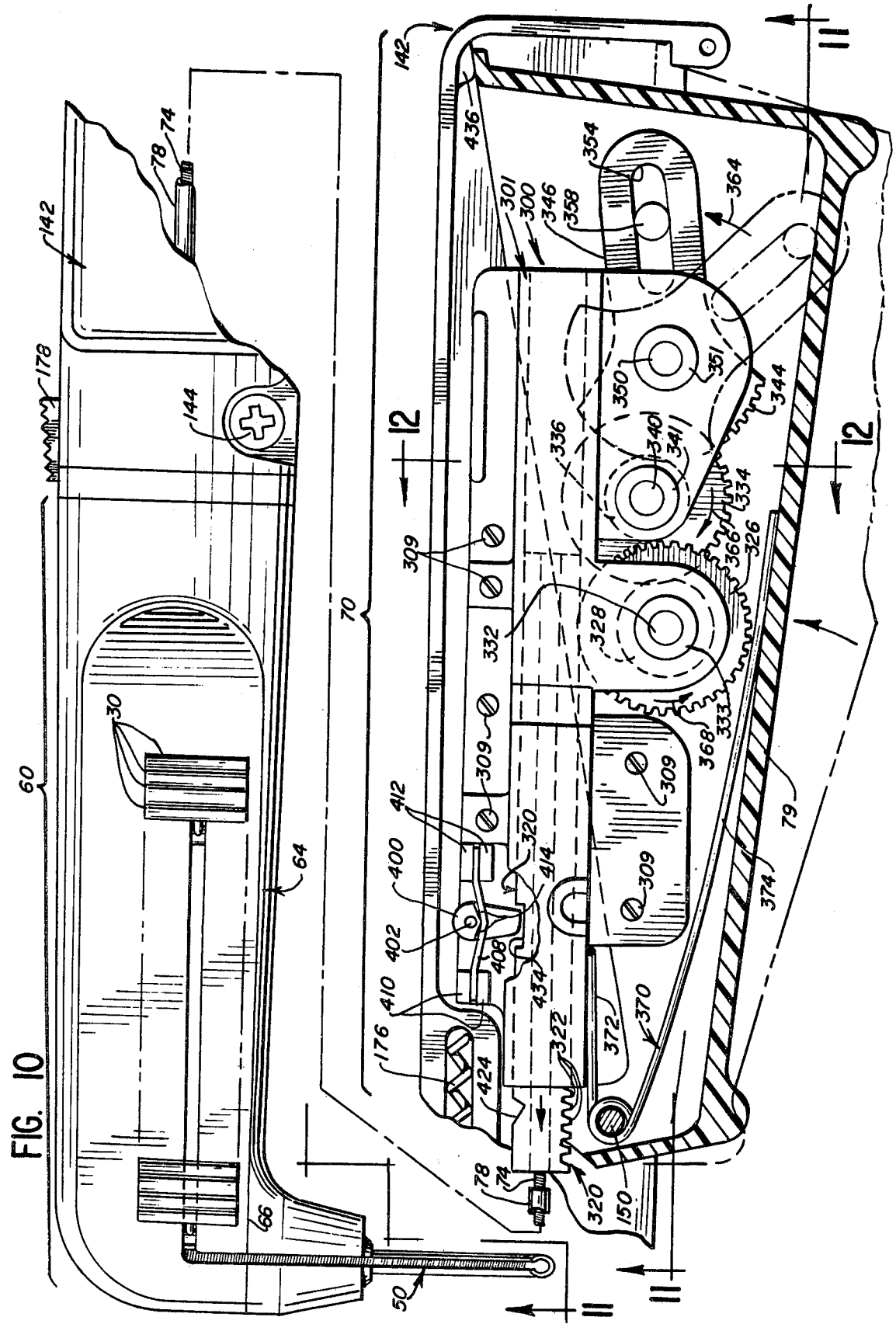

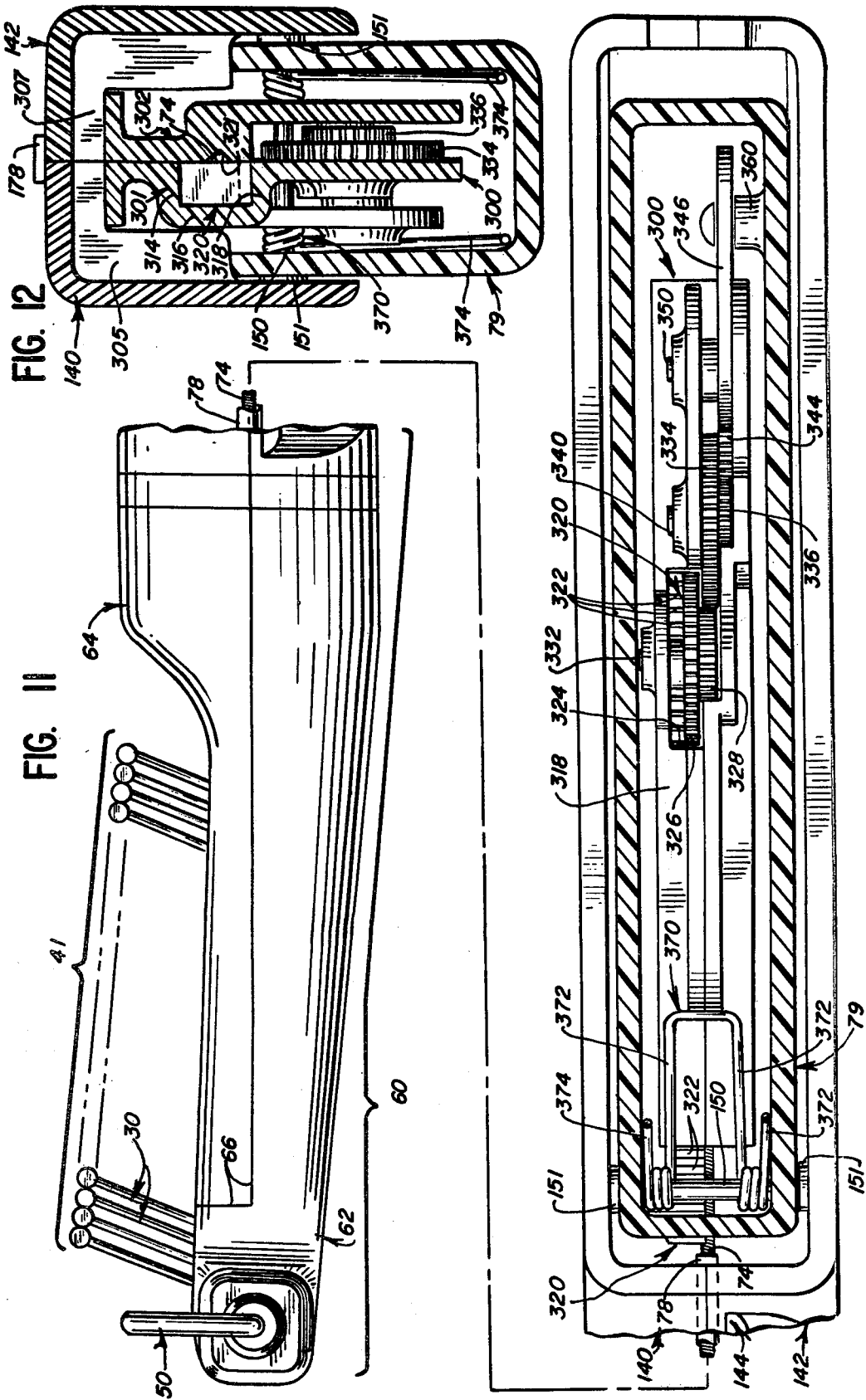

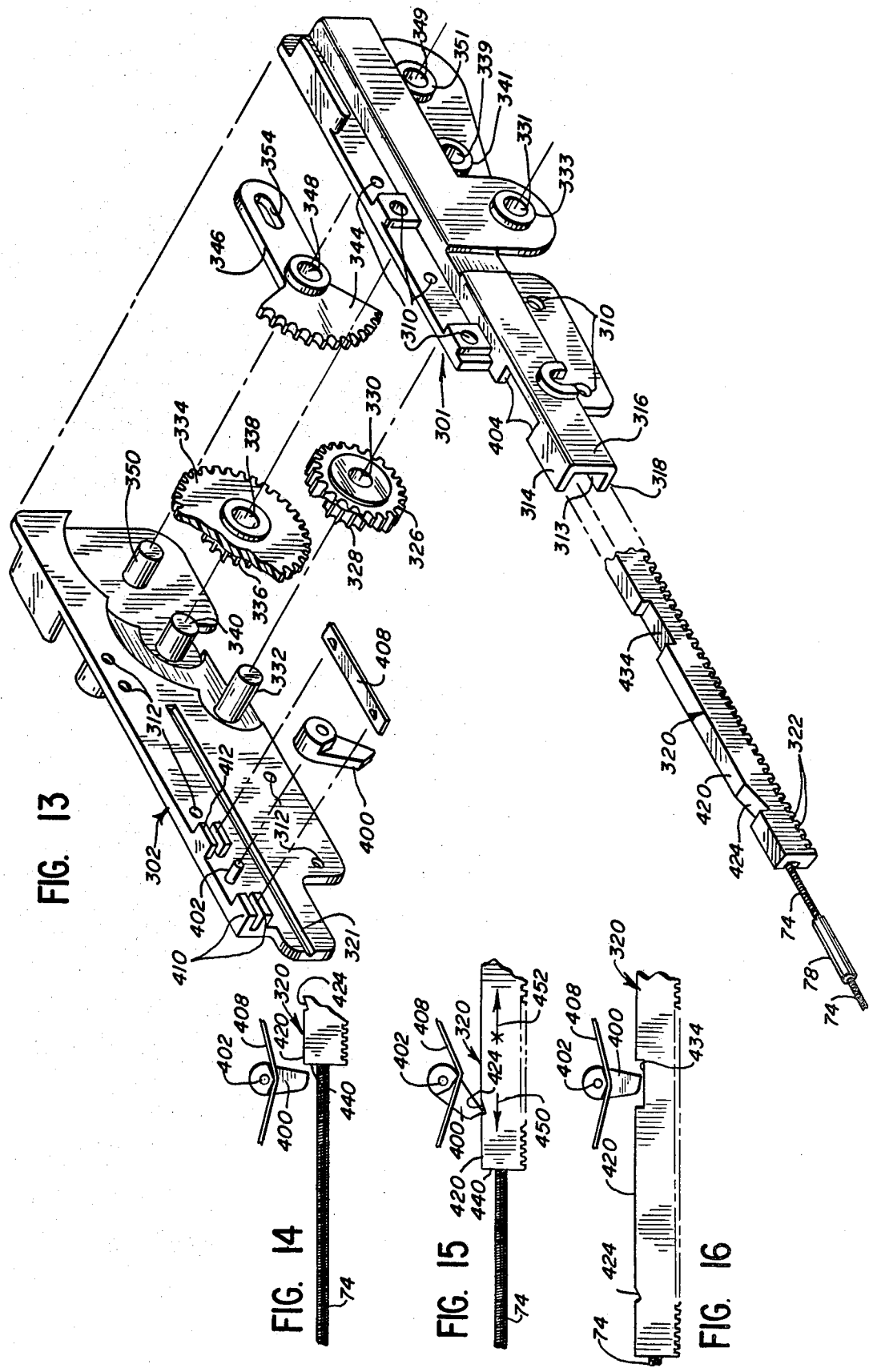

SURGICAL INSTRUMENT WITH ROTATABLE FRONT HOUSING AND LATCH MECHANISM

DESCRIPTION

Technical Field

This invention relates to hand-operated surgical instruments, and more particularly to instruments that are adapted to be held by the surgeon in a particular orientation during use.

Background of the Invention

A variety of hand-held surgical instruments have been proposed and/or are in use today for effecting a variety of surgical procedures or other operations that are performed upon human or animal anatomical structures, such as bone and tissue, including skin, muscle, and fascia. Some of these instruments are also used to effect certain operations with, or on, foreign bodies or prosthetic devices that may be implanted in, or carried by, a human or animal subject. Examples of the above-described instruments include instruments for applying ligating clips to blood vessels, bone crushing instruments, pin cutting instruments, instruments for applying staples or other types of fasteners to tissue, and the like.

Many of these types of instruments are held in one hand by the surgeon and include one or more movable operating elements or members (e.g., crimping or gripping jaws) which are located toward an end of the instrument that is spaced from, or remote from, the surgeon's hand. Typically, such an instrument includes an operating handle mechanism, which may be a reciprocative element, a single lever, a pair of scissors-type levers, or other suitable mechanism. The operating member or members are connected through mechanical linkages to the handle mechanism. Manipulation of the handle mechanism by the surgeon causes the desired movement of the operating member or members so as to effect the desired operation, such as applying a ligating clip to a blood vessel, cutting a pin, crushing a bone, inserting a staple or fastener into tissue, and the like.

A method has been proposed for using an instrument or device for closing wounds or surgical incisions in mammalian tissue with fasteners made from flexible and resilient biocompatible material which may be either absorbable or nonabsorbable in body tissue. One such type of device for applying such a fastener to tissue is generally disclosed in U.S. Pat. No. 4,006,747.

The device disclosed in U.S. Pat. No. 4,006,747 generally includes a slotted hollow needle in which is carried a portion of the fastener, a rigid plunger for pushing the fastener along the needle and into the tissue, and a mechanism for moving the plunger into the needle and then for withdrawing the plunger from the needle.

Other devices of the type disclosed in U.S. Pat. No. 4,006,747 suitable for use in applying various types of fasteners are disclosed in U.S. Pat. Nos. 3,470,834, 3,103,666, 2,069,878, 3,494,004, 3,399,432, 3,518,729, and Design Patent No. 313,418.

Other devices for applying fasteners in a non-surgical situation are disclosed in U.S. Pat. Nos. 3,209,422 and 3,733,657.

Prior to the disclosure in U.S. Pat. No. 4,006,747 of the method for applying a fastener simultaneously through a needle and tissue, procedures for the manual application of sutures or fasteners through tissue with needles or needle-like elements were known. Examples of such sutures and needles are disclosed in U.S. Pat. Nos. 3,636,956, and 3,716,058.

The inventors of the present invention have determined that it would be desirable to provide a structure for use in a wide variety of surgical instruments, including in the fastener applying devices described above, that permits the front portion of the instrument to be rotated about the longitudinal axis of the instrument. Further, it would be desirable to provide a mechanism for releasably locking the front portion of the instrument in a specific orientation relative to the rear portion of the instrument. This would enable the surgeon to conveniently maintain the operating member (e.g., a needle, jaw, and/or pusher element) on the front portion of the instrument in a desired orientation relative to the rear portion of the instrument.

Also, it would be advantageous if instruments of the class described could be provided with the structure of the type described wherein the structure was relatively small and compact so as to permit incorporation of the structure in a housing that could be easily grasped and manipulated with one hand by the surgeon.

SUMMARY OF THE INVENTION

The present invention provides a structure for surgical instruments that permits the front of the instrument to be rotated to a selected orientation relative to the rear portion of the instrument. In a preferred form disclosed herein, the present invention contemplates a novel mechanism for, and other modifications to, the fastener applying device of the general type disclosed in U.S. Pat. No. 4,006,747.

In general, the novel mechanism can be used in those hand-operated surgical instruments that have a rear portion and a front portion from which at least one movable operating member extends or is adapted to extend. The front housing and the rear housing are mounted together to permit relative rotation of the housings about a common longitudinal axis. In the preferred embodiments of the invention, the front housing has an annular portion defining a plurality of cavities arranged at selected azimuthal locations about the longitudinal axis. The cavities are in the form of bores arranged at circumferentially spaced locations in the annular portion.

The rear housing carries a slidably disposed engaging member or pin that is normally biased by a spring to a forwardly projecting position. In the forward position, the pin is received in one of the bores of the front housing for engaging the front housing and locking the front housing in a fixed position relative to the rear housing.

The pin also includes a thumb actuating button projecting from the exterior of the housing. The pin is guided within a channel in the rear housing which permits the pin to be moved rearwardly out of the front housing by the surgeon pushing the button rearwardly. When the pin is fully retracted from the front housing, the biasing spring is compressed and the front and rear housings may be rotated relative to each other about the longitudinal axis to a selected new orientation. Release of the button permits the spring to bias the pin forwardly again into a selected bore in the front housing to again lock the front and rear housings against further relative rotation.

In a preferred form of the invention, the above-described housing rotation structure is incorporated in a fastener applying device that is adapted for closing a wound or incision in tissue with a fastener. The fastener is of the type comprising a filament member terminated on at least one end by an anchoring means. The other end may also have an anchoring means. The fastener is applied by the device to remain in the tissue with the filament member transversing the wound or incision through the tissue to maintain the tissue in approximation at the wound or incision.

Preferably, the device includes a rear housing in which, inter alia, the handle and actuating system is disposed. The device includes a front housing from which a hollow needle extends. The needle has a distal end adapted for piercing the tissue. The needle defines a passage therein for receiving an anchoring means of the fastener. The passage in the needle extends along the length of the needle from an entrance aperture to a discharge aperture at the distal end of the needle. The needle also defines a slot communicating with the passage along the length of the needle from the entrance aperture to the discharge aperture. The slot is adapted to receive a portion of the fastener filament member.

The device also includes an operating member in the form of an elongate pusher member adapted to reciprocate in the needle passage and adapted to engage the anchoring means of the fastener for pushing the fastener along the needle.

The actuating mechanism includes a rack gear to which the pusher member is secured, a pinion engaged with the rack gear, a train of spur gears for driving the pinion, and a gear segment meshing with one of the spur gears and operably connected to a handle that is pivotally mounted to the device. Movement of the handle effects the desired movement of the pusher member.

The length of the pusher member and the movement stroke effected by the actuating mechanism is selected so that the pusher member can be reciprocated between (1) a retracted position spaced inwardly from the discharge aperture of the needle to permit admission of a fastener into the needle and (2) an extended position outwardly along the needle relative to the retracted position wherein the fastener is ejected from the discharge aperture of the needle by the pusher member.

The housing rotation feature described above permits the needle, which extends from the front housing, to be positioned at a desired orientation relative to the rear housing (by which the surgeon holds the device) during operation of the device.

Additionally, the device includes a fastener magazine with a feeder member for automatically feeding the surgical fasteners into alignment with the needle and for preventing actuation of the device after all of the fasteners have been ejected from the device.

The device also includes a pawl mechanism for preventing repeated actuation of the flexible pusher operating member unless and until the operating member has been moved through the full design range of movement.

The present invention resides in the combination, construction, arrangement, and disposition of various component parts and elements incorporated in the device in accordance with the principles of this invention. The present invention will be better understood and important features others than those specifically enumerated above will become apparent when consideration is given to the following details and description which, when taken in conjunction with the annexed drawings, describes, discloses, illustrates, and shows a preferred embodiment of the present invention and what is presently considered and believed to be the best mode of practicing the principles of the invention.

Other embodiments and modifications may be suggested to those having the benefit of the teachings herein, and such other embodiments and modifications are intended to be reserved, especially as they fall within the scope and spirit of the subjoined claims.

BRIEF DESCRIPTION OF THE DRAWINGS

In the accompanying drawings forming part of the specification, and in which like numerals are employed to designate like parts throughout the same.

FIG. 3 is an enlarged, partial cross-sectional view taken generally along the plane 3—3 in FIG. 1 but modified to show the instrument in the unactuated or released mode;

FIG. 4 is a partial cross-sectional view taken generally along the planes 4—4 in FIG. 3;

FIG. 5 is a cross-sectional view taken generally along the plane 5—5 in FIG. 3;

FIG. 6 is a fragmentary, enlarged, cross-sectional view taken generally along the plane 6—6 in FIG. 3;

FIG. 7 is a fragmentary, enlarged, cross-sectional view taken generally along the plane 7—7 in FIG. 3;

FIG. 8 is a fragmentary, enlarged, cross-sectional view taken generally along the plane 8—8 in FIG. 4;

FIG. 9 is an enlarged, cross-sectional view taken generally along the plane 9—9 in FIG. 3;

FIG. 10 is an enlarged, partial cross-sectional view taken generally along the plane 3—3 in FIG. 1 but modified to show the instrument in a fully actuated mode with a fastener having been ejected from the needle;

FIG. 11 is an enlarged, partial cross-sectional view taken along the planes 11—11 in FIG. 10 to show only the rear portion of the instrument in cross section;

FIG. 12 is a cross-sectional view taken along the plane 12—12 in FIG. 10;

FIG. 13 is an exploded perspective view of the gear housing and internal components that are disposed in the rear portion of the instrument; and FIGS. 14-16 are simplified diagrams showing the operation of the full stroke compelling mechanism of the instrument.

DESCRIPTION OF THE PREFERRED EMBODIMENT

This invention may be used in many different forms. This specification and the accompanying drawings disclose only one specific form as an example of the use of the invention. The invention is not intended to be limited to the embodiment illustrated, and the scope of the invention will be pointed out in the appended claims.

The precise shapes and sizes of the components herein described are not essential to the invention unless otherwise indicated.

For ease of description, the device of this invention will be described in an orientation as illustrated in the figures and terms such as upper, lower, horizontal, etc., will be used with reference to this orientation. It will be understood, however, that the device of this invention may be manufactured, stored, transported, used, and sold in an orientation other than the position described.

In the following description, reference is made to the industry standards of the American Iron and Steel Institute, 1000 16th Street, N.W., Washington, D.C. U.S.A. 20036. These standards will be designated by the common initial letters "AISI" followed by a suffix comprising additional alphanumeric characters and the standards are understood to be those in effect as of Aug. 1, 1981.

For ease of understanding the present invention, the invention is illustrated in a preferred embodiment comprising a hand-held, hand-operated device for closing a wound or incision in tissue with a particular type of fastener. Before describing in detail the various components of the fastener applier device, the fastener and the general method of applying the fastener with the device will first be described. This will be followed by a detailed description of the elements comprising the fastener applying device.

THE FASTENER

Figure 1:
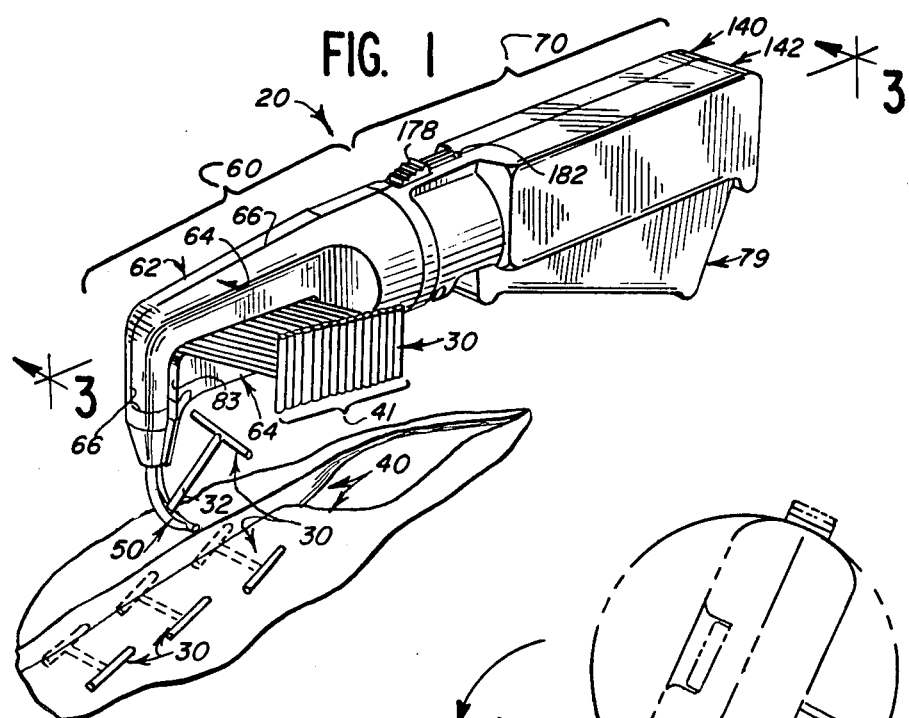
FIG. 1 is a perspective view of a hand-held surgical fastener applier instrument of the present invention shown being used to close an incision in tissue in a surgical procedure.

FIG. 1 illustrates a method of applying, with a fastener applier device 20 of the present invention, a plurality of fasteners 30 to skin or other tissue 40 in a surgical procedure.

The fastener 30 is identical to the flexible fastener disclosed in the U.S. Pat. No. 4,006,747 and reference is directed thereto for a complete description of such a fastener. Briefly, with reference to FIG. 2c of the drawings annexed hereto, the fastener 30 includes a filament member 32 terminated at one end by first anchoring means or rod-shaped head 36 and at the other end by an identical second anchoring means or rod-shaped head 34.

The fastener 30 is conveniently H-shaped and constructed of a flexible and resilient biocompatible material which may be either absorbable or non-absorbable in body tissue. As disclosed in detail in the above-referenced U.S. Pat. No. 4,006,747, the fastener 30 may be constructed of any of the wide variety of materials or combinations of materials. For example, materials such as nylon and polypropylene can be used to mold nonabsorbable fasteners 30 with good results. Also, copolymers of glycolide and lactide can also be used with good results and have the additional advantage of being absorbable in tissue and thus are particularly well suited for internal use in applications where long-term maintenance of wound support is not required.

As best illustrated in FIG. 1, a series of fasteners 30 are typically placed in close proximity along the length of the wound or incision to effectively close the wound or incision and enable natural healing to proceed. Nonabsorbable fasteners are removed from the tissue closures by snipping off one head and withdrawing the fastener with the opposite head.

METHOD OF APPLYING THE FASTENER

Figure 2A:
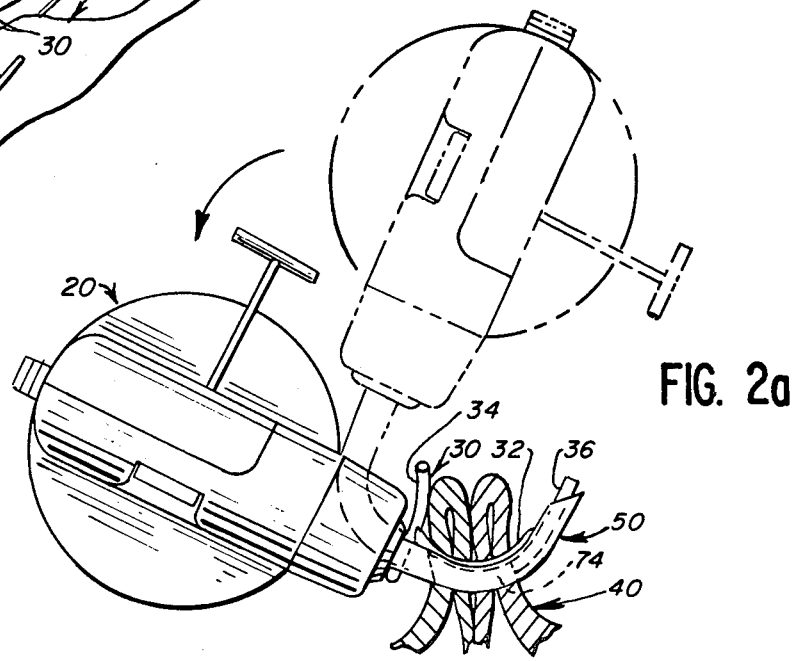
FIG. 2a is an end view of the fastener applier instrument of FIG. 1 and a fragmentary, cross-sectional view of the tissue with the instrument shown in dashed line in a first portion as the needle pierces the tissue and with the instrument shown in solid line in a moved position while placing a fastener across the incision.
Figure 2B:
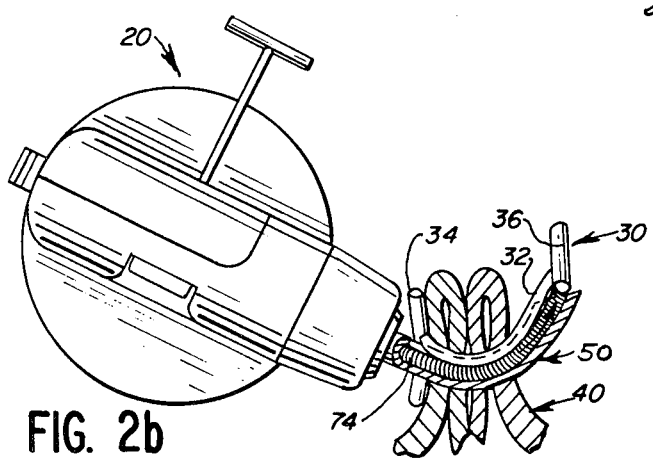
FIG. 2b is a view similar to FIG. 2a but showing a stage in the surgical procedure that is later than that illustrated in FIG. 2a and showing the needle in partial cross-section.
Figure 2C:
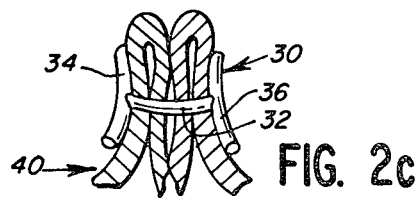
FIG. 2c is a fragmentary, cross-sectional view of the tissue after the fastener applier instrument has been removed so as to leave the fastener in place across the incision.

As best illustrated in FIG. 2c, and as more fully described in the above referenced U.S. Pat. No. 4,006,747, the fastener 30 is used to close a wound or incision by first folding over the tissue 40 on each side of the wound or incision and then approximating the folded over portions. Next, with the folded tissue held, as by grasping it with forceps, the flexible fastener 30 is temporarily bent or deformed and inserted through the skin on both the sides of the wound or incision. This can be effected with a fastener applying device, such as the device 20 illustrated in FIGS. 1–2b, in the general manner disclosed in the above-referenced U.S. Pat. No. 4,006,747.

Specifically, the device 20 is provided with means for holding a plurality of fasteners 30 in an aligned row 41 as best illustrated in FIG. 1. The device 20 includes a hollow needle 50 adapted for receiving one rod-shaped head of the fastener 30 as best illustrated in FIG. 1. The needle 50 also has a longitudinally extending slot through which the filament 32 of the fastener projects. The device 20 is adapted to feed one fastener 30 at a time into the hollow, slotted needle 50 and to push the fastener along the needle.

As best illustrated in FIG. 2a, the needle 50 is passed into the approximated and folded tissue 40 from a point on one side of the wound and on through the tissue until the tip of the needle 50 exits the tissue on the opposite side of the wound.

The path of the needle 50 through the tissue is not unlike that followed in conventional suturing. While closing a wound by conventional suturing, the needle and a length of attached suture are passed completely through the tissue. The hollow needle in the present case is inserted only far enough to penetrate through the tissue to form an open communication with both sides of the wound.

As best illustrated in FIGS. 2a and 2b, the applier device 20 includes a flexible pusher member 74 (visible in FIG. 2b) that is adapted to reciprocate within the curved, hollow needle 50 and to engage and push an end of the fastener's rod-shaped head 36 through the hollow needle until it is discharged from the tip of the needle 50 on the far side of the wound. Then the needle 50 is withdrawn from the tissue while the fastener 30 is restrained in the tissue 40 by the head 36 on the far side of the wound. The fastener is thus left in the tissue 40 with the filament 32 of the fastener 30 traversing the wound along the path created by the needle 50 and with the two anchoring means (the heads 34 and 36) engaging the restraining the surface of the tissue 40 on either side of the wound or incision.

Although the needle 50 is illustrated in FIGS. 1–2b as being curved and as guiding a flexible pusher member 74, it is to be realized that the device 20 of the present invention may have a substantially straight needle guiding a rigid pusher member as in the embodiment described and illustrated in the above-discussed U.S. Pat. No. 4,006,747 and as disclosed in U.S. Pat. Nos. 3,470,834; 3,103,666; 2,069,878; 3,494,004; 3,394,432; 3,518,729; and Design Pat. No. 313,418.

It has been found that when the needle 50 is curved and also projects downwardly and outwardly to one side of the fastener applier device 20 as illustrated in FIG. 1, certain advantages are realized. Specifically, the use of a needle having this type of orientation on the device 20 permits the surgeon to use a hand movement that is substantially similar to that used when applying conventional sutures with conventional suture needles. This is desirable since most surgeons have developed, and have become accustomed to, such hand movement when applying conventional sutures. Therefore, the adoption and use of the fastener applier device 20 of the present invention by a surgeon is more readily facilitated.

FIGS. 1–2c illustrate the tissue or skin 40 being folded over once at each side of the wound. It is to be realized that such a fold is not necessary when closing a wound or incision with the fastener 30 as installed by the fastener applier device 20 of the present invention. Specifically, reference is directed to FIGS. 2 and 4 of the above-discussed U.S. Pat. No. 4,006,747 for illustrations of the use of a fastener identical to the fastener 30 disclosed herein but wherein the tissue on each side of the wound is not folded over.

FASTENER APPLIER DEVICE MAGAZINE AND NEEDLE STRUCTURE

As best illustrated in FIG. 1, the device 20 has a generally elongate housing having a front or magazine portion 60 that contains the fastener row 41 and needle 50 and having a rear portion 70 that houses the actuating mechanism. A handle, trigger, or handle means 79 extends from the rear housing portion 70.

The first or front end portion 60 will next be described in detail with reference to FIGS. 1 and 3–5. With reference to FIG. 1, the front end portion 60 of the device preferably comprises two molded portions or pieces, piece 62 and piece 64. Each piece is preferably molded from a suitable material. For example, the pieces 62 and 64 may be molded from a polycarbonate resin such as that sold in the United States of America under the trademark or trade name Merlon M40 F by the Mobay Chemical Corporation.

Pieces 62 and 64 are mated together about a parting plane 66 (see in FIG. 1 as the line running the length of the device 20). The pieces 62 and 64 are joined together by suitable means such as screws, adhesive, or other bonding means (not illustrated). In FIG. 3, the first piece 62 is viewed along its parting plane and is seen to define an arcuate channel 72 at the front end in which the flexible pusher member 74 is slidably disposed. The flexible pusher member 74 is preferably constructed from AISI 316 L Series stainless steel 30 gauge wire wound in a helical configuration having a radius slightly less than the radius of the arcuate channel 72.

The flexible pusher member 74 extends rearwardly in the device 20 from the front end of the housing magazine portion 60 through a hollow tube 78 into the rear portion 70 and is operatively engaged with the actuating means within the housing rear portion 70 as will be explained in detail hereinafter.

As best illustrated in FIGS. 1 and 4, the piece 64 of the housing front end portion 60 defines an L-shaped slot 83, the base leg portion of which L-shaped slot 83 is in registry with the arcuate channel 72 of the mating housing piece 62. The other leg of the L-shaped slot 83 receives the row 41 of fasteners 30.

The front end of the housing piece 62 has a generally conical configuration as best illustrated in FIGS. 1 and 5 and carries a needle holder insert 84 as best illustrated in FIG. 3. The needle holder insert 84 has a generally cylindrical configuration with a slot 86 in registry with the channel 72 of the housing piece 62.

The needle 50 is secured by a suitable means within the needle holder insert 84 and projects from the distal end thereof as best illustrated in FIGS. 3 and 5. The needle 50 is hollow and extends outwardly away from the housing piece 62. The distal end of the needle 50 is preferably angled or sharpened (as best illustrated in FIG. 2a) to facilitate the piercing of tissue.

The needle 50 defines a passage 80 as best illustrated in FIG. 5. The passage 80 extends along the length of the needle 50 from the entrance aperture of the needle within the needle holder insert 84 to the discharge aperture at the distal end of the needle 50. The needle 50 also defines a slot 82 along its length as best illustrated in FIG. 5. The slot 82 is coextensive with the passage 80 and therefore extends from the entrance aperture of the needle 50 within the needle holder insert 84 to the discharge aperture at the distal end of the needle 50. The slot 82 communicates with the passage 80 along the entire length of the needle 50. The passage 80 of the needle 50 is adapted to receive one of the fastener anchoring means or rod-shaped heads (head 36 in FIG. 2a). The slot 82 of the needle 50 is adapted to receive a portion of the filament 32 of the fastener 30.

In a preferred form of the invention illustrated, the needle 50 and the needle holder insert 84 are both preferably fabricated from a suitable metal, such as AISI 420 stainless steel. Preferably then the insert 84 and needle 50 are welded together to form an integral assembly which is then suitably secured within the conical portion of the housing piece 62.

As best illustrated in FIGS. 3 and 4, the front portion 60 of the fastener applier device 20 also includes a magazine 100 for holding a plurality of fasteners 30 in the row 41 and for feeding the fasteners 30 seriatim into the channel 72 defined in the front housing piece 62. Specifically, as best illustrated in FIGS. 3, 4, and 6, the magazine 100 includes a base member 102 defining a slot 103 and having a pair of angled retainer flanges 104 adapted to receive the fasteners 30. Specifically, the anchor means or rod-shaped head 36 of each fastener 30 is slidably received within the flanges 104 and on top of the slotted member 102. The fastener filament member 32 extends out of the magazine through the space defined between the flanges 104.

The magazine 100 is mounted within the housing portion 62 as best illustrated in FIGS. 3 and 4. Specifically, the rear end of the magazine 100 has a rearwardly extending tab 110 by which the magazine 100 is secured with a screw 112 to the housing portion 62. At the front end of the magazine 100, the magazine 100 has an off-set but forwardly extending tab 114 which is retained under a cross wall 116 of the housing portion 62.

Slidably disposed within the magazine 100 on top of the bottom member 102 is a feeder member 120 (FIGS. 4 and 7) which has a downwardly depending tab 122 disposed through the central slot 103 of the magazine bottom member 102.

The downwardly depending tab 122 of the feeder member 120 is biased forwardly with a band spring 126 as best illustrated in FIG. 4. As best illustrated in FIGS. 3, 7, and 8, the band spring has two oppositely coiled portions 130 which are disposed within a retainer or guide wall 132. The central portion of the band spring 126 is pulled outwardly from the coiled portions 120 and extends underneath and along the length of the magazine 100 to the feeder member tab 122 with which it is engaged. Thus, the feeder member 120 is continuously biased forwardly to push the fasteners 30 toward the channel 72 defined in the housing portion 62.

The guide tube 78, the arcuate channel 72 in the housing piece 62, and the channel 86 in the needle holder insert 84 all function as a guide means in the housing that serves to guide the movement of the flexible pusher member 74 into alignment with the entrance aperture and a passage 80 of the needle 50. Further, that portion of the channel 72 in the housing piece 62 immediately adjacent the front end of the magazine 100 can be regarded as defining a "fastener dispensing region" aligned with the entrance aperture of the needle 50 for accommodating admission of the fastener rod-shaped head 36 in registry or alignment with the entrance aperture and passage 80 (FIG. 5) of the needle 50.

As best illustrated in FIGS. 3 and 4, the width of the channel 72 in the housing portion 62 has a configuration and dimensions sufficient to accommodate the rod-shaped end of just one of the fasteners 30 at the front end of the magazine 100. The head 36 of the fastener is fed from the magazine 100 into the channel 72 just forward of the flexible pusher member 74 when the flexible pusher member 74 is in a fully retracted position. The channel 72 of the housing piece 62 thus serves to guide and align the flexible pusher member 74 and the rod-shaped head 36 of the fastener with the passage 80 of the needle 50. When the flexible member 74 is moved forwardly toward the needle 50 by suitable actuating means (described in detail hereinafter), the rod-shaped head 36 of the fastener 30 travels along the channel 72 of the housing portion 62, along the channel 86 of the needle holder insert 84, and finally through the needle 50. The flexble pusher member 74 is moved forwardly until its leading end pushes the fastener rod-shaped head 36 out of the needle passage 80 (as illustrated in detail in FIG. 2b).

After the rod-shaped head 36 of the fastener has been ejected from the needle discharge aperture, the flexible pusher member 74 is retracted back to the position illustrated in FIG. 3 (by means described in detail hereinafter). As long as the flexible pusher member 74 extends beyond the front of the magazine 100, the next fastener 30 in the magazine 100 is prevented from being fed from the magazine to the channel 72 in the housing piece 62. However, as soon as the flexible pusher member 74 has returned to a point just behind the magazine 100 as illustrated in FIG. 3, the next fastener 30 is urged forwardly into the channel 72 of the housing piece 62. Thus, the fastener applier device 20 is ready to apply the next fastener.

The magazine 100 is uniquely designed to prevent actuation of the instrument after all of the fasteners 30 have been ejected and when the magazine 100 is thus empty. Specifically, with continued reference to FIGS. 3 and 4, it can be seen that the forward or distal end portion of the feeder member 120 will project into the channel 72 after the last fastener has been ejected and after the flexible pusher member 74 has been fully retracted from the fastener dispensing region in front of the magazine 100. The fastener feeder member 120 will be maintained in this position at the forward end of the magazine by the band spring 126. Consequently, any attempt to move the flexible pusher member 74 forward from the fully retracted position illustrated in FIG. 3 will fail since the distal end of the flexible pusher member 74 will necessarily impinge against the end of the fastener feeder member 120 projecting into the channel 72. As will become evident hereinafter, this prevents the handle 79 from being actuated and thus serves as an indication that all of the fasteners have been ejected from the instrument.

REAR HOUSING AND ACTUATING HANDLE MOUNTING STRUCTURE

As best illustrated in FIGS. 3 and 4, the rear housing portion 70, which contains the actuating means and the handle or trigger 79, is fabricated from two halves or pieces 140 and 142. In FIG. 3, a forward part of the rear housing piece 140 is broken away along the parting plane to show the other rear housing piece 142. As best illustrated in FIGS. 3 and 4, the housing pieces 140 and 142 are suitably secured together, as with screws, one of which screws 144 is visible in FIG. 4. These pieces 140 and 142 are preferably molded from the same materials as the housing front portion 60 described above.

Preferably the handle or trigger 79 is molded from the same material as the other housing pieces and is pivotably mounted to the rear housing portion 70 about a pivot shaft 150 as illustrated in FIGS. 3, 10, and 12. The shaft 150 passes through the handle 79 as best illustrated in FIG. 12 and is journalled on either end in molded bearing structures 151 projecting inwardly from the rear housing pieces 140 and 142.

To operate the trigger 79, the device 20 is typically grasped with the palm of the hand at the top of the rear housing 70 (as viewed in FIG. 3) with the fingers and/or thumb extending down to the trigger 79. The trigger 79 is operably connected with an actuating means, described hereinafter in detail, to move the flexible pusher member 74 from the retracted position (illustrated in FIG. 3) to the extended position (illustrated in FIG. 2b) wherein the fastener 30 is ejected from the discharge aperture of the needle 50.

FRONT AND REAR HOUSING ROTATION STRUCTURE

As best illustrated in FIGS. 3 and 9, the rear housing piece 142 has a generally cylindrical portion 160 at the forward end of the rear housing. The front housing piece 62 has an annular portion or flange 161 in which the cylindrical portion 160 is received at the rear of the front housing piece 62. The cylindrical portion 160 has an aperture 163 through which the guide tube 78 passes. As best illustrated in FIGS. 3 and 4, the cylindrical portion 160 carries a spring clip or retaining ring means 164 in a groove for holding the cylindrical portion 160 within the flange 161 of the front housing piece 62. The ring 164 causes the rear housing pieces 140 and 142 to be biased forwardly with the cylindrical portion 160 until the rear housing pieces 140 and 142 engage the front housing pieces 62 and 64. This serves to hold together the rear housing 70 and front housing 60.

As best illustrated in FIG. 9, the annular portion 161 of the front housing piece 62 includes a plurality of circumferentially spaced cavities or bores 170 at selected azimuthal locations about the longitudinal axis of the instrument. These bores 170 are adapted to receive an engaging member or indexing pin 172 carried in a channel 174 of the rear housing piece 142. The channel 174 functions as a guide means for guiding the pin 172 for reciprocating movement into and out of one of the bores 170. The indexing pin 172 is biased forwardly into one of the bores 170 by means of a compression spring 176 which is disposed within the bore 174 between the end of the bore and the indexing pin 172.

The indexing pin has an upwardly extending member or button 178 adapted to be engaged by the thumb of the surgeon operating the fastener applier device 20. The button 178 has a T-shape when viewed from the side as in FIG. 3 and is connected to the pin 172 by a vertically extending stem portion. As best illustrated in FIG. 1, the button 178 is adapted to reciprocate within a channel 182 defined in the mating housing pieces 140 and 142. When the pin 172 is biased forwardly into one of the bores 170 by the spring 176 as illustrated in FIG. 3, the stem portion of the button 178 abuts the annular portion 161 and prevents further forward movement of the pin 172.

The front housing portion 60 and the rear housing portion 70 can be rotated relative to each other. Specifically, the front housing piece 62 (together with the front housing piece 64 connected to the piece 62) can be rotated together relative to the rear housing portion 70 about the cylindrical portion 160 when the indexing pin 172 is pulled rearwardly out of engagement with the bores 170. When the desired orientation of the needle 50, relative to the trigger 79, is obtained, the indexing pin 172 is released by the surgeon. The indexing pin 172 is then forced forwardly by the spring 176 against the front housing piece 62. An additional slight rotational movement of the front housing portion 60, in either direction of rotation, may be necessary to align one of the bores 170 with the indexing pin 172, whereupon the indexing pin 172 is driven further forwardly by the spring 176 into a bore 170 to thereby lock the front housing portion 60 relative to the rear housing portion 70.

The housing rotation feature described above permits the needle, which extends from the front housing, to be positioned at a desired orientation relative to the rear housing by which the surgeon holds the device. This accommodates the application of fasteners to tissue in various parts of the body and reduces the possibility of the surgeon having to assume an awkward position relative to both the patient and device while operating the device.

The above-described housing rotation and latching structure has been illustrated as part of the fastener applier device 20. It is to be realized however, that the rotation and latching structure may be used with other types of instruments that have an operating member extending from or adapted to be extended from, a front housing portion.

THE ACTUATING MECHANISM

The rear housing portion 70 contains the novel actuating mechanism or means for reciprocating the flexible pusher member 74 between the retracted position and the extended position. The actuating mechanism is next described in detail with reference to FIGS. 10-16 which illustrate the interior structure of the rear housing portion 70 of the fastener applier device.

FIG. 10 shows the molded rear housing piece 142 viewed along its parting plane with some interior components cut away and with some interior components illustrated in cross section. For ease of illustration in FIG. 10, the front housing portion 60 has not been shown in cross section.

As best illustrated in FIGS. 10, 11 and 12, the actuating mechanism includes an internal gear housing 300 disposed in the rear housing portion 70. As best illustrated in FIG. 13, the gear housing 300 includes two pieces, piece 301 and piece 302, which are adapted to be placed together in mating relationship and to contain between them various other components of the actuating mechanism described in detail hereinafter.

As best illustrated in FIG. 12, the pieces 301 and 302 of the gear housing 300 are held in place between the rear housing pieces 140 and 142. To this end, rear housing piece 140 has an inwardly projecting wall 305 and rear housing piece 142 has an inwardly projecting wall 307. Either one or both of the gear housing pieces 301 and 302 may be further secured to the inwardly projecting walls 305 and 307 by suitable means, such as by screws as discussed hereinafter.

The gear housing pieces 301 and 302 may be secured to each other with suitable screws 309 (FIG. 10). To this end, the gear housing piece 301 is provided with appropriate receiving bores 310 and the gear housing piece 302 is provided with suitable threaded bores 312 aligned with the bores 310 of the gear housing piece 301. If desired, some of the bores 312 in the gear housing piece 302 may be unthreaded to permit the screws 309 to pass through the gear housing piece 302 and into suitable threaded bores (not illustrated) in the inwardly projecting wall 307 (FIG. 12) of the rear housing piece 142. Of course, other suitable means may be provided for securing the gear housing pieces 301 and 302 together and/or for mounting the gear housing pieces 301 and 302 in the rear housing portion 70 of the device. Such other means may include snap-fit structures, rivets, adhesives, and the like.

Preferably, the gear housing pieces 301 and 302, and the internal components disposed therein, are molded from a thermoplastic polymer material to provide a lightweight assembly. For example, the gear housing pieces 301 and 302 may be molded from a polycarbonate resin such as that sold in the United States of America under the trademark or trade name Merlon M40 F by the Mobay Chemical Corporation.

As best illustrated in FIG. 12, the gear housing pieces 301 and 302 extend downwardly in the device and project into the handle 79. The handle 79 has a generally U-shaped cross section so as to permit at least the lower portions of the gear housing 300 to be contained within the handle 79.

With reference now to FIGS. 12 and 13, the gear housing piece 301 is seen to have an open channel 313 (FIG. 13) defined by a top wall 314, a sidewall 316, and a bottom wall 318. The channel 313 defined by the three walls is designed to receive a gear rack 320. The gear rack 320 is retained within the channel 313 by the other gear housing piece 302 and is guided for reciprocating movement within the channel 313.

The flexible pusher member 74 extends from the front housing portion 60, out of the end of the guide tube 78, and into the gear rack 320 to which it is secured. The gear rack 320 thus functions as a carrier or carrier member for the pusher member 74. Gear housing piece 302 defines a wall channel 321 having a substantially V-shaped cross section and which is disposed generally in registry with the rack 320 so as to accommodate the pusher member 74 mounted to one side of the rack 320 as best illustrated in FIGS. 12 and 13.

The rack 320 is generally elongate member that has a plurality of gear teeth 322 projecting downwardly toward the channel bottom wall 318. As best illustrated in FIG. 11, the channel bottom wall 318 defines a slot 324 below the rack 320. This provides an access to the rack teeth 322 from below the channel bottom wall 318.

Mounted below the rack 322 is a pinion 326 and the pinion teeth engage or mesh with the rack teeth 322. The pinion 326 is part of a unitary structure that includes a first spur gear 328 that is coaxially aligned with the pinion 326. The unitary structure of the pinion 326 and first spur gear 328 defines a bore 330 (FIG. 13) by means of which the unitary gear structure is rotatably disposed on a fixed shaft 332 projecting outwardly from the gear housing piece 302. The distal end of the shaft 332 is received in a bore 331 defined in a boss 333 on the gear housing piece 301.

Rearwardly of the first spur gear 328 is a second spur gear 334 formed as a unitary structure with a third spur gear 336 that is coaxially aligned with the second spur gear 334. The second spur gear 334 meshes with the first spur gear 328. The unitary structure of the second spur gear 334 and third spur gear 336 together define a bore 338 by which the unitary gear structure is rotatably disposed on a fixed shaft 340 projecting outwardly from the gear housing piece 302. The distal end of the shaft 340 is received in a bore 339 defined in a boss 341 on the gear housing piece 301.

Behind the third spur gear 336 is a sector gear 344 which is mounted to one end of an arm 346. The sector gear 344 and arm 346 define a bore 348 by which the unitary structure of the sector gear and arm is rotatably mounted to a fixed shaft 350 projecting outwardly from the gear housing piece 302. The distal end of the shaft 350 is received in a bore 349 defined in a boss 351 on the gear housing piece 301.

The arm 346 defines a slot 354 at one end opposite the sector gear 344. The handle 79 includes a pin 358 (FIG. 10) projecting inwardly from a boss 360 (FIG. 11) and which is received within the slot 350 (FIG. 10) of the arm 346.

As best illustrated in FIG. 10, when the handle 79 is moved from the unactuated or released position (illustrated in dashed lines) to the fully actuated position (illustrated in solid lines), the pin 358 moves upwardly with the handle 79 and moves within the arm slot 354 to pivot the arm 346 and connected sector gear 344 in the counterclockwise direction indicated by arrow 364. This causes the sector gear 344 to rotate the third spur gear 336 and the connected second spur gear 334 in the clockwise direction indicated by arrow 366. This drives the first spur gear 328 and the pinion gear 326 in the counterclockwise direction as indicated by the arrow 368. As a result, the pinion 328 (connected to the first spur gear 326) drives rack 320 forwardly in the gear housing 300 to move the flexible pusher member 74 from the retracted position to the extended position.

The rack, pinion, spur gears, sector gear, and arm together comprise an actuating or actuator means or mechanism by which the device effects movement of an operating member such as the flexible pusher 74. The first, second, and third spur gears 326, 334 and 336, respectively, can be regarded as a gear train which, along with the sector gear 344 and arm 346, can be regarded generally as a gear means associated with the handle 79 for engaging and rotating the pinion 328 in response to movement of the handle 79.

As best illustrated in FIGS. 10, 11, and 12, a spring 370 is provided to bias the handle 79 from the fully actuated position to the unactuated or released position. Specifically, the spring 370 is wound around the pivot shaft 150 and has two upper legs 372 (FIGS. 10 and 11) forming a U-shaped structure bearing against the bottom of the gear housing 300. The spring 370 also has two lower legs 374 bearing against the inside bottom portion of the handle 79 as best illustrated in FIGS. 10 and 12.

A novel mechanism is provided for compelling a full stroke of the handle 79 before the handle is permitted to be returned to the unactuated or released position. In the embodiment illustrated, this has the effect of preventing the flexible pusher member 74 from pushing more than one fastener 30 out of the needle at a time. As will next be explained in detail, the flexible pusher member is prevented from returning to the retracted position behind the fastener magazine 100 (FIG. 3) unless and until the pusher member 74 has first been moved to the completely extended position.

Specifically, as best illustrated in FIGS. 10 and 13–16, a pawl 40 is pivotally mounted to the gear housing piece 302 on a pin 402 above the rack 320. As best illustrated in FIG. 13, the upper wall 314 of the rack receiving channel 313 in the gear housing piece 301 has an opening 404 that permits the distal end of the pawl 400 to extend into the channel 313. The pawl 400 is biased to a vertical neutral orientation by a spring plate 408 which is mounted to the gear housing piece 302 at one end between a pair of outwardly projecting flanges 410 and at the other end between a pair of outwardly projecting flanges 412. As best illustrated in FIG. 10, the upper portion of the pawl 400 is formed with a step or shoulder defined by two front faces 414 that together form an obtuse angle. The spring 408 bears against the faces 414 to urge the pawl 400 into the generally vertical neutral orientation illustrated in FIGS. 10, 14, and 16. The pawl 400 is adapted to be pivoted from the vertical neutral position in a first direction (clockwise as viewed in FIG. 10) in a second direction (counterclockwise as viewed in FIG. 10).

As best illustrated in FIG. 13, the rack 320 has a cam means or engaging surface 420 which is defined between a front end wall 440 on one end and a recess 434 on the other end. The recess 434 is deep enough to accommodate the pawl 400 in the vertical neutral orientation when the recess 434 is in registry below the pawl 400 (FIGS. 10 and 16). In this position illustrated in FIG. 10, the rack 320 has been moved to the limit of its forward movement (to the left when viewing FIG. 10) wherein the flexible pusher member 74 is in the fully extended position for discharging a fastener from the end of the needle. A detent means or notch 424 is defined in the cam means or surface 420 for a purpose described in detail hereinafter.

Note that the pusher member fixed guide tube 78 extends rearwardly to a point just short of the furthest point reached by the forward end of the rack 320 (FIG. 10). The forward movement of the rack 320 and of the connected pusher member 74 is terminated by the upper end of the handle 79 engaging a suitable stop or abutment 436 at the back of the rear housing piece 142 as best illustrated in FIG. 10.

When the surgeon releases the actuated handle 79, the handle 79 is urged by the spring 370 to pivot about the shaft 150 (in the clockwise direction as viewed in FIG. 10). As the handle 79 rotates to the released position (indicated in dashed lines in FIG. 10), the pin 358 carried by the handle 79 causes the sector gear 344 to pivot about the shaft 350 (clockwise as viewed in FIG. 10). This causes the gear train (the third, second, and first spur gears 336, 334, and 326, respectively,) to drive the pinion 328 to move the rack 320 to a position rearward of the forward position illustrated in FIG. 10.

As the rack 320 moves rearwardly, the edge of the cam means 420 at the recess 434 engages the pawl 400 and pivots the pawl 400 away from the neutral orientation (FIG. 10) in the second direction (counterclockwise as viewed in FIG. 10) to permit the rack 320 to move without the rack notch 424 engaging the pawl 400.

When the handle 79 has pivoted to the fully released position (indicated by dashed lines in FIG. 10), the rack 320 has been moved completely past the pawl 400 as best illustrated diagramatically in FIG. 14. When the rack front end wall 440 has moved past the pawl 400, the pawl 400 is free to assume the vertical neutral orientation illustrated in FIG. 14. It is to be realized that the rack 320 could be made longer if desired and a second recess, similar to the first recess 434, could be provided at the forward end of the cam means or surface 420 on the rack 320 to permit the pawl 400 to assume the vertical orientation illustrated in FIG. 14 when the rack 320 is in the rearwardmost position.

In any case, if the handle 79 is now pivoted back toward the fully actuated position, the rack 320 begins to move forward. As illustrated diagrammatically in FIG. 15, the rack 320 moves forward in the direction of the arrow 450. The edge of the cam means 420 at the rack front wall 440 engages the pawl 400 and pivots the pawl 400 away from the neutral orientation in the first direction (clockwise as viewed in FIG. 15). The pawl 400 is maintained in that pivoted position by engagement with the top engaging surface or cam means 420 of the rack 320. With continued forward movement of the rack 320, the detent means or notch 424 is brought into alignment or registry with the distal end of the pivoted pawl 400. The pawl 400 falls into notch 424 as illustrated in FIG. 15. At this point, the rack 320 cannot be moved rearwardly (in the direction of arrow 452 in FIG. 15) since the pawl 400 prevents such movement. Only continued forward movement of the rack 320 is thus permitted.

Eventually, when the handle 79 is pivoted to the fully actuated position (illustrated in solid lines in FIG. 10), the rack 320 is in the position diagrammatically illustrated in FIG. 16. At this point, the pusher member 74 is fully extended in the needle 50 (FIG. 10) and the pawl 400 is urged to the vertical neutral orientation by the spring 408 where the pawl 400 is permitted to assume that neutral orientation owing to the recess 434 in the top of the rack 320 at the end of the cam means 420.

With the pawl 400 in the vertical neutral position, the handle 79 may be released. The rack 320 will then be driven rearwardly (to the right as viewed in FIG. 16). The cam means 420 will engage the pawl 400 and cause the pawl 400 to be pivoted away from the neutral orientation in the second direction (counterclockwise as viewed in FIG. 16). When the handle 79 has been pivoted to its fully released or unactuated position (indicated by dashed lines in FIG. 10), the rack 320 has moved past the pawl 400 to again permit the pawl 400 to assume the vertical neutral orientation beyond the rack front end wall 440 as illustrated in FIG. 14.

With reference to FIGS. 13-16, the distance between the recess 434 and the notch 424 and the location of the pawl 400 are selected so that the rack 320 cannot be moved rearwardly from an extended position beyond the fastener magazine 100 until the flexible pusher member 74 has been moved to the end of the needle 50. At this point, the rack recess 434 would be in registry with the pawl 400 (FIG. 16) so that the rack 320 would then be free to be moved rearwardly to return the flexible pusher 74 to the fully retracted position behind the fastener magazine 100 and ready to engage another fastener fed by the magazine to the dispensing region in front of the distal end of the flexible pusher 74.

Although the actuating mechanism described above is particularly useful when incorporated in the fastener applier device 20 for applying fasteners 30, it is to be realized that the actuating mechanism may be incorporated in other instruments. Such other instruments may have flexible or rigid pusher members for pushing a foreign body, other than a fastener, into tissue.

Also, such other instruments may instead incorporate one or more other types of movable operating elements or members. Such other instruments may include instruments for applying ligating clips to blood vessels, bone crushing instruments, pin cutting instruments, and instruments for applying staples to tissue.

From the foregoing, it will be observed that numerous variations and modifications may be effected without departing from the true spirit and scope of the novel concept of the invention. It is to be understood that no limitation with respect to the specific apparatus and method illustrated herein is intended or should be inferred. It is, of course, intended to cover by the appended claims all such modifications as fall within the scope of the claims.

What is claimed is:

1. In a hand-operated surgical instrument that has a front housing portion, means carried by said front housing portion for sequentially applying a plurality of surgical fasteners;

a rear housing portion, and actuating means carried by said rear housing portion for intermittently activating the fastener applying means;

the improvement comprising:

means associated with said front and rear housing portions for permitting rotation of one of said housing portions relative to the other, said means comprising an annular portion on said front housing defining a bore and a cylindrical portion on said rear housing received in said bore;

one of said front and rear housing portions defining a plurality of cavities arranged at selected azimuthal locations about the axis of rotation; and the other of said front and rear housing portions having at least one slideably disposed engaging member for being received in any one of said cavities and engaging said one housing portion, said other housing portion defining a guide means for guiding said engaging member for reciprocating movement into and out of said cavities, whereby said portions may be rotated relative to each other when said engaging member is out of the cavities;

said other housing portion further including a biasing means for biasing said engaging member into one of said cavities after the front and rear housing portions have been relatively rotated to align one of said cavities with said engaging member whereby the housing portions are locked against further rotation.

2. The improvement in accordance with claim 1 further including a retaining ring means on said cylindrical portion for biasing said rear housing portion against said front housing portion.

* * * * *